United States Patent
Zeskind et al.

(10) Patent No.: US 7,335,874 B2
(45) Date of Patent: Feb. 26, 2008

(54) METHOD AND APPARATUS FOR GENERATING A CIRCULARLY POLARIZED ILLUMINATION BEAM

(75) Inventors: Benjamin J. Zeskind, Cambridge, MA (US); Paul Matsudaira, Newton, MA (US); Daniel Ehrlich, Somerville, MA (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/331,981

(22) Filed: Jan. 13, 2006

(65) Prior Publication Data

US 2006/0209408 A1   Sep. 21, 2006

Related U.S. Application Data (60) Provisional application No. 60/723,656, filed on Oct. 4, 2005, provisional application No. 60/678,458, filed on May 5, 2005, provisional application No. 60/663,171, filed on Mar. 18, 2005.

(51) Int. Cl.
*G02F 1/01* (2006.01)
*H01J 40/14* (2006.01)

(52) U.S. Cl. .................. 250/225; 359/352; 359/386; 359/483; 359/497

(58) Field of Classification Search ............... 250/225; 359/350, 351, 352, 494, 497, 501, 629, 638, 359/385, 386, 388, 483; 362/19, 227
See application file for complete search history.

(56) References Cited

U.S. PATENT DOCUMENTS 4,670,854 A * 6/1987 Mossberg et al. ........... 708/816

OTHER PUBLICATIONS

Davies., Ultra-violet Microspectrography of Living Tissue Culture Cells, Part I, Radiation Measurements, Discussion of the Faraday Society, vol. 9, 1950, pp. 442-449.

(Continued)

*Primary Examiner*—Georgia Epps
*Assistant Examiner*—Francis M LeGasse, Jr.
(74) *Attorney, Agent, or Firm*—Wolf, Greenfield & Sacks, P.C.

(57) ABSTRACT

A method and apparatus for illuminating a subject with deep UV light and detecting 2-dimensional image information, e.g., a transmission image, fluorescence image, reflected light image, etc. The subject may be illuminated with a light pulse having a duration of 2 seconds or less and one or more components with a wavelength of between about 150 nm to about 300 nm. The light pulse may be arranged so as to minimize or eliminate any detrimental effect on the functioning of the subject, e.g., on a living cell. A concentration, mass, quantum yield, absorbance or other characteristics of one or more compounds in the subject may be determined based on one or more 2-dimensional images obtained of the subject. An illumination beam having left and right circularly polarized components may be generated, e.g., for circular dichroism analysis of a subject.

19 Claims, 7 Drawing Sheets

OTHER PUBLICATIONS

Walker et al., Ultra-violet Microspectrography of Living Tissue Culture Cells, Part II, Microspectrographic Studies of Living Cells and Ultraviolet-irradiated Chick Fibroblasts, Discussions of the Faraday Society, vol. 9, 1950, pp. 461-470.

Lichtscheidl et al., Investigation of the protoplasm of Allium cepa inner epidermal cells using ultraviolet microscopy, European Journal of Cell Biology, vol. 43, 1987, pp. 93-97.

Lang-Pauluzzi, The behaviour of the plasma membrane during plasmolysis; a study by UV microscopy, Journal of Microscopy, vol. 198, Pt. 3, Jun. 2000, pp. 188-198.

Lillard et al., Temporal and spatial monitoring of exocytosis with native fluorescence imaging microscopy, Journal of Neuroscience Methods, vol. 75, 1997, pp. 103-109.

Lobenstine et al., Fluorescence Detected Circular Dichroism of Proteins with Single Fluorescent Trytophans, Journal of the American Chemical Society, vol. 103, 1981, pp. 4963-4940.

Tan et al., Neurotransmitter Imaging in Living Cells Based on Native Fluorescence Detection, Anal. Chem., vol. 67, 1995, pp. 2575-2579.

Judge et al., An ultraviolet fluorescence-based method for identifying and distinguishing protein crystals, Acta Cryst., vol. D61, 2005, pp. 60-66.

Palmer et al., Autoflurescence Spectroscopy of Normal and Malignant Human Breast Cell Lines, Photchemistry and Photobiology, vol. 78(5), 2003, pp. 462-469.

Yuan et al., Tryptophan Fluorescence Quenching by Methionine and Selenomethionine Residues of Calmodulin: Oritentation of Peptide and Protein Binding, Biochemistry, vol. 37, 1998, pp. 3187-3195.

Kunnil et al., Fluorescence quantum efficiency of dry *Bacillus globigii* spores, Optics Express, vol. 13, No. 22, Oct. 2005, pp. 8969-8979.

Mickols, Scanning differential polarization microscope: Its use to image linear and circular differential scatering, Rev. Sci. Instrum., vol. 59(6), Jun. 1988, pp. 867-872.

Muller et al., The measurement of the fluorescence detected circular dichroism (FDCD) from a chiral Eu(II) system, Chem. Commun., 2005, pp. 3615-3617.

Tinoco Jr., et al., Fluorescence Detected Circular Dichroism. Theory, Journal of the American Chemical Society, Oct. 1976, vol. 98:21, pp. 6453-6456.

Lunde, et al., UV microscopy at 280 nm is effective in screening for the growth of protein microcrystals, J. Appl. Cyrst., vol. 38, 2005, pp. 1031-1034.

Caspersson, Cell Growth and Cell Function, 1950, W.W. Norton & Company, New York, pp. 56, 57 and 66-71.

Walker, P.M.B., Ultraviolet Absorption Techniques, Physical Techniques in Biological Research, vol. III Cells and Tissues, 1956, Academic Press, New York, pp. 401-487.

Du, et al., Calcium Measurements in Perfused Mouse Heart: Quantitating Fluorescence and Absorbance of Rhod-2 by Application of Photon Migration Theory, Biophysical Journal, vol. 80, Jan. 2001, pp. 549-561.

Mackey et al., Optical material stress measurement using two orthogonally polarized sinussoidally intensity-modulated semiconductor lasers, Measurements Science and Technology, vol. 13, 2002, pp. 179-185.

http://www.renishaw.com/client/product/UKEnglish/PGP-181. shtml, printed Feb. 1, 2006, 4 pages.

http://microspectra.com, printed Feb. 1, 2006, 1 page.

http://www.tnpinstruments.com, printed Feb. 1, 2006, 1 page.

Engle et al., Double-Beam Vibrating Mirror Flying Spot Scanning-Integrating Microspectrophotometer, Rev. Sci. Instrum., vol. 39, 1968, pp. 307-312.

Freed et al., Development of the Vibrating-Mirror Flying Spot Microscope for Ultraviolet Spectrophotometry, Annals of the New York Academy of Sciences, vol. 97, Art 2, 1962, pp. 412-430.

Williams, Instrumentation for Time Lapse Ultraviolet Television Microscopy, Annals of the New York Academy of Sciences, vol. 97, Art 2, 1962, pp. 358-363.

* cited by examiner

Fig. 8 (units in mg)

Fig. 9 (units in mg)

Fig. 10

METHOD AND APPARATUS FOR GENERATING A CIRCULARLY POLARIZED ILLUMINATION BEAM

This application claims priority to U.S. applications Ser. No. 60/663,171, filed Mar. 18, 2005, 60/678,458, filed May 5, 2005, and 60/723,656, filed Oct. 4, 2005, which are hereby incorporated by reference in their entirety.

BACKGROUND

1. Field of Invention

This invention relates to methods and apparatus for imaging, such as that used in microscopy.

2. Related Art

Imaging is widely used in the study of relatively small subjects, such as living cells and biological tissue. Using a microscopy device, much can be learned by viewing a cell or other material under high magnification. Often, the cell or other subject may be treated with a stain or other compounds to help identify particular features. Different illumination conditions are also used to more clearly show portions of a subject. For example, a subject may be illuminated with a particular type of light to provide better contrast when using a stain. Most microscopy devices are equipped to accommodate variations in illumination and other features to provide desired viewing characteristics.

In general, ultraviolet (UV) light is not used in microscopy to image live cells or other living subjects because the UV illumination may cause death of the living subjects during imaging. For example, the UV illumination may cause damage to nucleic acid or other compounds in the cell such that normal cell function is disrupted to the point that the cell can no longer remain viable.

SUMMARY OF INVENTION

In one aspect of the invention, a method and apparatus are provided to enable imaging of a living cell or other similar subject using UV illumination and without causing necrosis or otherwise having a significant effect on functioning of the subject. For example, aspects of the invention allow for microscopy imaging of a live cell using deep UV (DUV) light, e.g., having a wavelength of about 150 nm to about 350 nm. Moreover, the cell may be repeatedly imaged under DUV conditions over a relatively long time span, such as hours, days or weeks, without causing necrosis or other detrimental effect on the cell so as to affect its normal functions during the study period. By allowing for deep UV imaging without necrosis or other significant effect on functioning, aspects of the invention provide scientists and others with the ability to view images of live subjects under illumination conditions that were previously unavailable to them.

As will be apparent from the description below, aspects of the invention are not limited to imaging live cells or other subjects. To the contrary, other aspects of the invention allow for imaging or other study of any suitable subject whether live, dead or never living (as in the case of proteins or other compounds). For example, aspects of the invention may be used with any biological material, including tissue samples, organs or organ samples, spores, viruses, biopsy samples, tumor samples, fixed cells, etc.

In one aspect of the invention, a method for imaging a subject includes providing a subject, illuminating the subject with a light pulse having a wavelength of about 150 nm to about 300 nm and a time duration of about 2 seconds or less, and detecting illumination that results from interaction of the light pulse with the subject to capture 2-dimensional image information for at least a portion of the subject. Illumination that results from interaction of the light pulse with the subject may be illumination that is transmitted through the subject, that is reflected from the subject, that is diffracted by the subject, that is emitted by a fluorescent or other compound in the subject in response to being excited by the light pulse, or other illumination that is caused by the light pulse being incident on the subject.

In another aspect of the invention, an apparatus for imaging a subject includes an illumination system that illuminates the subject with a light pulse having a wavelength of about 150 nm to about 300 nm and a time duration of about 2 seconds or less, and a detector that detects illumination that results from interaction of the light pulse with the subject so as to capture 2-dimensional image information of at least a portion of the subject. In one embodiment, the subject may be living, such as a living cell, and illuminating the subject with the light pulse does not result in significant effect on functioning of the living subject. In some cases, the living subject may be illuminated and image information detect multiple times without causing significant effect on functioning of the living subject. For example, a living cell may be illuminated and imaged several times over the course of a motility study (e.g., over several hours, days or weeks) without affecting motility functions of the cell. In one embodiment, the subject may be illuminated using brightfield illumination of the subject in a microscopy or endoscopy device.

In another aspect of the invention, a method for analyzing a subject includes providing a subject including at least first and second different compounds, where the compounds are absorbent of light in a wavelength range of between about 150 nm to about 300 nm. The subject may be illuminated with light in the wavelength range, and illumination of a first wavelength or range of wavelengths that results from interaction of the light with the subject may be detected so as to capture first 2-dimensional image information of at least a portion of the subject. Illumination of a second wavelength or range of wavelengths that results from interaction of the light with the subject may also be detected so as to capture second 2-dimensional image information of at least a portion of the subject. The first and second 2-dimensional image information may be used to determine concentrations of the first and second compounds in the subject. In accordance with aspect of the invention, the absolute or relative concentrations of two or more compounds may be determined based on two or more images captured of a subject, such as a cell or other biological material.

In another aspect of the invention, an apparatus for imaging a subject includes a support for a subject having at least first and second different compounds that are absorbent of light in a wavelength range of between about 150 nm to about 300 nm. An illumination system may be adapted to illuminate the subject with light of one or more wavelengths in the wavelength range. A detector may detect illumination at a first wavelength or set of wavelengths that results from interaction of the light with the subject so as to capture first 2-dimensional image information of at least a portion of the subject, and may detect illumination at a second wavelength or set of wavelengths that results from interaction of the light with the subject so as to capture second 2-dimensional image information of at least a portion of the subject. An analyzer may be adapted to determine concentrations of the first and second compounds in the subject based on the first and second 2-dimensional image information.

In one embodiment, the absolute and/or relative concentrations of the first and second compounds may be determined for a plurality of pixel or voxel locations in the subject. Using such information, an optical density or mass attributable to two or more compounds in the subject may be determined for each of a plurality of pixel or voxel locations in the subject. For example, the optical density or mass attributable to protein and nucleic acid may be determined for a cell based on image information captured of the cell. Such information may be visibly displayed in image form for the first and second compounds.

In another aspect of the invention, a method for analyzing a subject includes providing a subject having a compound that fluoresces in response to illumination of a suitable wavelength, and illuminating the subject with illumination of the suitable wavelength. Fluorescent illumination emitted by the compound in the subject may be detected so as to capture 2-dimensional fluorescent image information, and a quantum yield for the subject may be determined based on the 2-dimensional fluorescent image information. For example, in one embodiment, transmitted illumination may be detected so as to capture 2-dimensional transmission image information as well as the fluorescent image information. The quantum yield may be determined based on the 2-dimensional transmission image information and the 2-dimensional fluorescent image information. A same field of illumination of a same wavelength may be used for detecting the transmitted illumination and the fluorescent illumination, e.g., the subject may be illuminated using a diafluorescent illumination arrangement in a microscopy device. The absolute or relative quantum yield may be determined for the subject for a plurality of pixel or voxel locations.

In another aspect of the invention, a method for imaging a subject includes providing a subject including a living cell and/or a biological material other than artificially crystallized proteins, illuminating the subject with illumination having a wavelength of about 300 nm or less, and detecting autofluorescent illumination emitted by the subject that results from interaction of the illumination with the subject so as to capture 2-dimensional image information of at least a portion of the subject. In one embodiment, a portion of the subject that emits autofluorescent illumination includes tryptophan or tyrosine, where the subject may be a living cell.

In another aspect of the invention, a method for imaging a subject includes providing a subject, and illuminating the subject with left circularly polarized illumination having a wavelength of about 350 nm or less. Illumination that results from interaction of the left circularly polarized illumination with the subject may be detected so as to capture first 2-dimensional image information of at least a portion of the subject. In addition, the subject may be illuminated with right circularly polarized illumination having a wavelength of about 350 nm or less, and illumination that results from interaction of the right circularly polarized illumination with the subject may be detected so as to capture second 2-dimensional image information of at least a portion of the subject. The method may be performed using, at least in part, a microscopy and/or endoscopy device, e.g., to perform a circular dichroism analysis of the subject. In one embodiment, the subject may be illuminated using a diafluorescence illumination arrangement in a microscopy device.

In another aspect of the invention, an illumination system may include a first light source adapted to emit a first light component having a first linear polarization, and a second light source adapted to emit a second light component having a second linear polarization that is orthogonal to the first polarization. A controller may be adapted to provide control signals to the first and second light sources that cause the first and second light sources to emit the first and second light components so that the components are intensity-wise modulated 180 degrees out of phase relative to each other. An optical system may combine the first and second light components into a light beam and circularly polarize the first and second light components in opposite, left and right directions so that the light beam oscillates between left and right circular polarized light at a frequency. Such a system may be used to illuminate a subject for circular dichroism analysis, for example. In one embodiment, the first and second components may be squarewave modulated so as to be intensity-wise 180 degrees out of phase, thereby making the light beam oscillate between left and right circularly polarized light.

In another aspect of the invention, a method for forming an illumination beam includes providing a first light component having a first linear polarization and a first intensity-wise frequency, and providing a second light component having a second linear polarization that is orthogonal to the first polarization and has a second intensity-wise frequency that is 180 degrees out of phase with the first intensity-wise frequency. The first and second light components may be circularly polarized to have opposite, left and right circular polarization, and combined into a light beam that intensity-wise oscillates between left and right circular polarized light at a frequency.

These and other aspects of the invention will be apparent from the following description and claims.

BRIEF DESCRIPTION OF THE DRAWINGS

Aspects of the invention are described below with reference to the following drawings in which like numerals reference like elements, and wherein.

DETAILED DESCRIPTION

This invention is not limited in its applications to the details of construction and the arrangement of components set forth in the following description or illustrated in the drawings. Aspects of the invention are capable of other embodiments and of being practiced or of being carried out in various ways. For example, illustrative embodiments of the invention are described below with reference to use in a microscopy device. However, it should be understood that aspects of the invention may be used in other suitable systems for any suitable application. For example, aspects of the invention relate to a method and apparatus for forming a beam for circular dichroism analysis. While this aspect of the invention is described in conjunction with 2-dimensional imaging in a microscopy device, this aspect of the invention may be used in other applications, such as spectroscopy or non-imaging applications. Similarly, aspects of the invention could be used in an endoscope for medical applications on living humans. Similarly, aspects of the invention are described in conjunction with imaging a live cell without causing necrosis. However, aspects of the invention are not limited in this regard, and may in some cases cause necrosis of a living cell and/or may be used with dead cells or compounds that were never previously living. For example, aspects of the invention may be used with any biological material, including tissue samples, organs or organ samples, spores, viruses, biopsy samples, tumor samples, fixed cells, etc.

In one aspect of the invention, a subject may be illuminated with a light pulse including light of a wavelength of about 300 nm or less and having a time duration of 2 seconds or less so as to enable the capture of 2-dimensional image information for at least a portion of the subject. As used herein, a "light pulse" includes any suitable electromagnetic radiation (whether visible or not) of one or more wavelengths that is incident on the subject over a period of time. The intensity of the light may vary during the time period, e.g., between zero and a maximum intensity. For example, a "light pulse" may include light of a constant intensity over a time duration, or may vary regularly or irregularly during the time duration, e.g., include two or more relatively high intensity illumination events that are separated from each other by one or more relatively low intensity illumination events. Light for the pulse may be generated by any suitable source, such as one or more light emitting diodes (LEDs), a lamp source, laser or other. The light may be operated on by any suitable optical components, such as a mechanical chopper, shutter or other, e.g., to define a time duration for the light pulse, to collimate/focus/filter/etc. the light, and so on. The light pulse may provide a relatively large area of illumination for a subject (e.g., illuminate the subject using brightfield illumination), or may be provided as a relatively small spot or other shape that is scanned over portions of the subject. The time duration of the pulse is determined as an average time period that each imaged portion of the subject receives illumination from the light pulse for image information capture.

In one illustrative embodiment, a light pulse may provide brightfield illumination of the subject so as to allow the capture of 2-dimensional or 3-dimensional image information for at least a portion of the subject. For example, in a microscopy device, the subject may be illuminated using a relatively large area illumination field that is larger than the subject. Image information may be captured based on illumination that results from interaction of the brightfield illumination with the subject. As used herein, image information that results from interaction of the light pulse or other illumination with the subject refers to any detectable characteristic that results from the illumination of the subject. For example, a transmission image may be captured based on illumination that is transmitted through the subject, a fluorescence image may be captured based on fluorescence illumination that is emitted by one or more compounds in the subject as a result of being excited by the light pulse, a photoacoustic image may be captured based on detected sound energy that results from illumination of the subject by the light pulse, a reflection image may be captured based on illumination that is reflected from the subject and so on.

In accordance with various aspects of the invention, image information that is captured may be used in any suitable way to determine one or more characteristics of the subject. For example, in some embodiments, a quantum yield, concentration, mass or optical density (where optical density and absorbance are used interchangeably throughout this document) for one or more compounds in the subject may be determined based on 2-dimensional image information. These and other characteristics may be determined for each pixel or voxel location in a subject, which may be of any desired size. (A voxel is a volumetric region as opposed to a pixel, which refers to an areal region.) Quantum yield and/or mass and/or concentration information may be determined in a relative sense (i.e., relative to other portions of the subject) or in an absolute sense.

Figure 1:
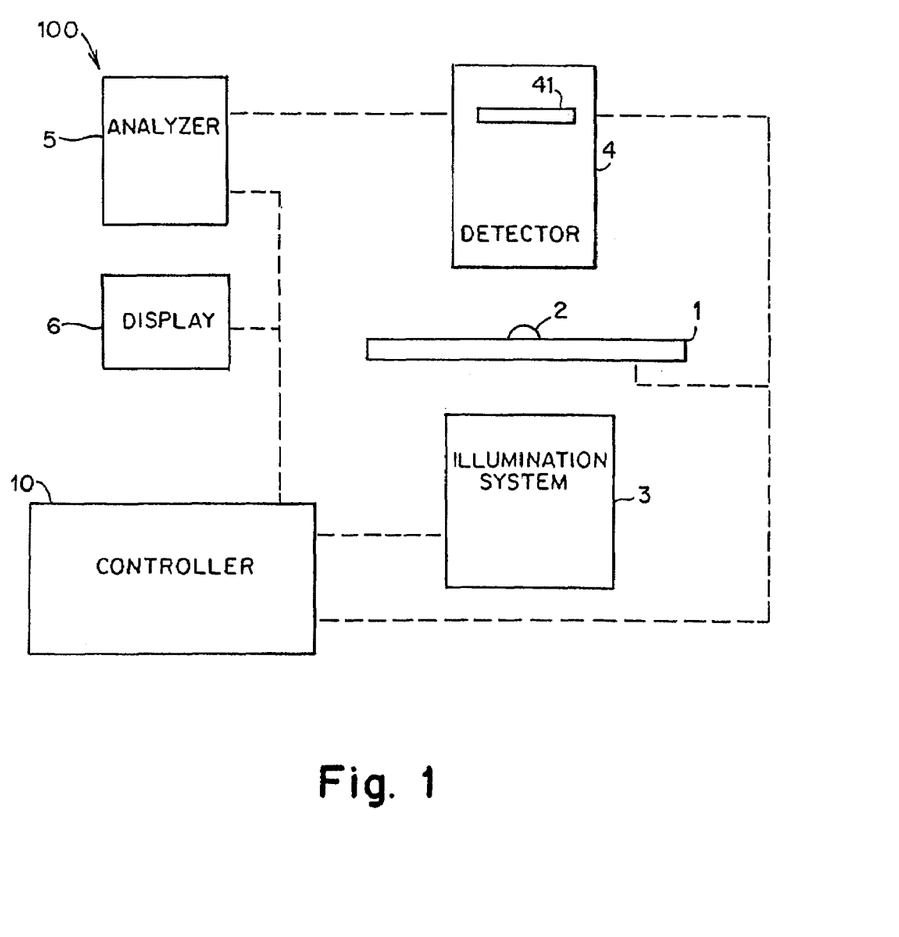
FIG. 1 is a schematic diagram of a microscopy device in accordance with aspects of the invention.

FIG. 1 is a schematic diagram of an illustrative microscopy device in accordance with aspects of the invention. In this embodiment, the microscopy device 100 includes a support 1 that supports a subject 2. The support 1 may be of any suitable type, such as a conventional microscopy stage and/or any other suitable arrangement to support a subject 2 for imaging. The support 1 may provide physical support for the subject 2, as well as perform other functions, such as heating or cooling the subject, moving the subject in one or more dimensions (e.g., to position the subject relative to a field of view), and so on. The subject 2 may be illuminated with light (i.e., any suitable type of electromagnetic radiation whether visible and/or non-visible) provided by an illumination system 3. In this illustrative embodiment, the illumination system 3 is shown to provide illumination from beneath the support 1, but as will be understood by those of skill in the art, the illumination system 3 may provide illumination to the subject 2 in any suitable way, such as from above the subject 2 and/or any other suitable direction. As will be discussed in more detail below, the illumination system 3 may include any suitable components such as those included in microscopy devices, e.g., lenses, mirrors, filters, a mechanical chopper or a shutter, one or more light sources, polarizers, beam combiners, beam splitters, fiber optics, etc. In this illustrative embodiment, the illumination system 3 includes at least a deep UV light source, such as an LED that emits light having a wavelength of less than 350 nm. Also, in this illustrative embodiment, the illumination system 3 includes at least one non-reflective optical component used to transmit DUV illumination to the subject 2. For example, a DUV LED may emit light of a wavelength of 350 nm or less, which is collimated, uniformized, focused and/or transmitted to a subject using one or more optical lenses, mirrors and so forth. For an LED light source, the LED may be controlled to emit light having a suitable pulse duration, thereby possibly avoiding the need to use a chopper or other device to control the time duration of illumination pulses. Pulse duration may also be controlled by using a scanning slit or other technique, as is known in the art.

In this illustrative embodiment, the microscopy device 100 includes a detector 4 that detects illumination that results from an interaction of the illumination from the illumination system 3 with the subject 2. The detector 4 may detect 2-dimensional image information, e.g., using a CCD or other electronic imaging device, a light sensitive film, or other similar device 41, from light that emanates from the subject 2 and is transited to the CCD or other device 41 via an objective lens and/or other optical components. (An objective or other optical components used to direct illumination to a CCD or other light sensitive device may form part of the illumination system 3 and/or the detector 4.) In this illustrative embodiment, the detector 4 includes a CCD 41 that detects light that may be transmitted through the subject, emitted by the subject, reflected by the subject, or otherwise emanates from the subject. The detector 4 may also include a viewing optic or other arrangement to allow an operator to view an image of the subject 2 and/or to view an image generated based on image information captured by the CCD 41. For example, when illuminating the subject 2 using DUV light, an operator will typically not be permitted to directly view light transmitted through or otherwise emanating from the subject, for to do so may cause damage to the operator's eyes. In such a case, the CCD 41 may capture image information, which is then used to generate a visible display (e.g., on an LCD or other suitable display device) that may be viewed by the operator. The display may be viewed by the operator using a ocular viewer or other arrangement.

The detector 4 may generate raw detected intensity values as image information, e.g., values that represent a relative or absolute light flux for each of a plurality of pixel locations of a CCD 41, and/or may provide image information that is generated from such raw image information. For example, the detector 4 may provide image information that includes interpolated pixel values, e.g., for individual malfunctioning or defective pixel sensors in a CCD. Alternately, the detector 4 may compress the image information using lossy or lossless techniques for transmission. The detector 4 may also perform A/D conversion on raw image information, e.g., to provide image information in a digital format. In short, the detector 4 may provide image information in any suitable way as is known in the art.

Image information may be provided from the detector 4 to an analyzer 5, which may use the image information to generate an image for a display 6, which may include a printer, a visible display device, an audio display device, and so on. As will be discussed in more detail below, the analyzer 5 may use the image information from the detector 4 to determine various characteristics of the subject 2, such as protein or nucleic acid concentrations (relative or absolute) for multiple pixel or voxel locations in the subject, an optical density for the subject at multiple pixel or voxel locations, an absorbance for the subject at multiple pixel or voxel locations, a relative or absolute quantum yield for the subject at multiple pixel or voxel locations, circular dichroism properties for the subject at multiple pixel or voxel locations, and others. In some cases, the analyzer 5 may be adapted to determine characteristics of the subject based only on image information from the detector 4; in other cases, the analyzer 5 may use image information and other information (e.g., provided by an operator via a suitable computer interface) to determine one or more characteristics.

Operation of the microscopy device 100 may be coordinated by a controller 10, which may, for example, provide control signals for the support 1, illumination system 3, detector 4, analyzer 5 and/or the display 6. As discussed in more detail below, the controller 10 may include any suitable components for performing its various input/output and/or control functions, such as a general purpose programmable computer or other data processing apparatus, one or more software modules, a user interface (such as a keyboard, display, touch screen, user pointing device, audio input/output devices), data storage devices, switches, relays, mechanical linkages, knobs, and so on. Moreover, the analyzer 5 may be incorporated into the controller 10, e.g., the analyzer 5 may include one or more software modules that operate on a data processing device in the controller 10. In the case of a microscopy device 100, the controller 10 may be incorporated physically as part of a structure that supports the illumination system 3 and detector 4 (e.g., include knobs, dials, filter slides, etc. used to control various portions of the microscopy device 100) and/or may be separate from the illumination system 3 and detector 4, e.g., may include a remote computer system in communication with the detector 4 via a wireless or wired LAN or other communications network. In accordance with an aspect of the invention, the subject 2 may be illuminated with a dose of light having a wavelength of about 300 nm or less and a duration of about 2 seconds or less to enable the capture of 2-dimensional image information regarding the subject. For example, the subject 2 may be illuminated by the illumination system 3 with a light pulse having a duration of about 100 ms (or less) and a wavelength of about 280 nm. Such DUV illumination may allow the detector 4 to capture transmission images, fluorescence images or other image information of the subject. For short duration light pulse illumination, the operation of the illumination system 3 and the detector 4 may be synchronized by the controller 10, e.g., so that the CCD 41 captures illumination from the subject at an appropriate time in relation to the generation of the light pulse by the illumination system 3. Multiple 2-dimensional images may be captured for different levels in the subject, thereby capturing 3-dimensional image information for the subject. For example, the detector 4 and/or associated optics (such as an objective lens) may be controlled to capture images for multiple planes in the subject that are displaced along the optical axis of the illumination beam. A first image may be captured for a first plane in the subject so that the depth of field for the detected image information is controlled to be relatively short. Thereafter, the detector 4 and/or associated optics and/or the position of the sample may be adjusted so that light from a second plane that is displaced along the optical axis relative to the first plane is captured, and so on. This type of process may be repeated for multiple planes, generating multiple 2-dimensional "slices" of image information for the subject.

In accordance with this aspect of the invention, illumination of the subject with light having a wavelength of about 300 nm or less may be adapted to avoid necrosis or other adverse affect on the functioning of a living cell or other biological organism. By "adverse affect on functioning" it is meant that the illumination of the subject does not directly cause the death or other undesirable change in function of the subject prior to an end of a study period. For example, in accordance with this aspect of the invention, a living cell undergoing a motility study may be illuminated and image information captured without causing a significant effect on the cell's functioning regarding motility, or a living cell undergoing division may be illuminated and image information captured without causing a significant effect on the cell's functioning regarding division. This is a significant advance over prior imaging approaches using illumination of 300 nm and under, which typically would cause cell death or otherwise affect the cell so that a proper study of certain cell functions would be impossible.

Figure 2:
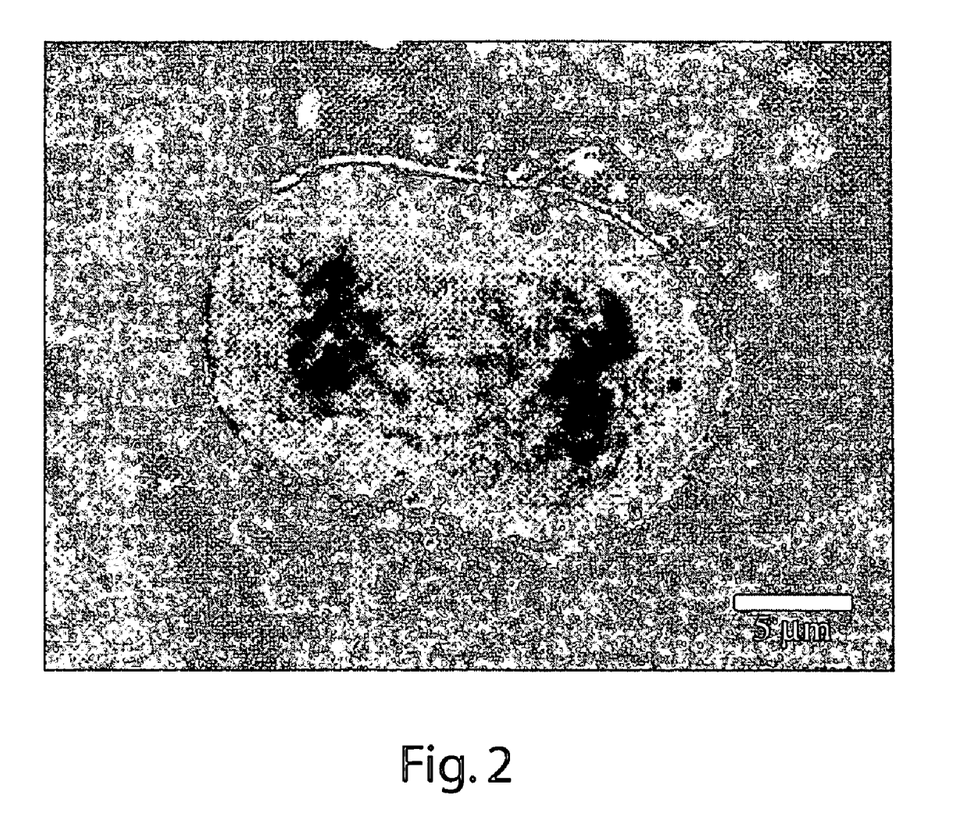
FIG. 2 shows an illustrative transmission image of a living subject.

In another aspect of the invention, illumination and imaging of a living cell or other biological organism may be repeated multiple times over an extended period without causing an adverse effect on functioning. For example, a living cell or group of cells may be repeatedly illuminated and imaged using light pulses having a wavelength of 300 nm or less over a period of several hours without significantly affecting cell functions. As a result, the cell may be imaged using DUV illumination over a period during which the cell functions in a normal or near normal way. In some illustrative embodiments, the illumination may have a wavelength in a range of 260-280 nm and may have a pulse duration of about 100 ms for each imaging event. FIG. 2 shows an illustrative transmission image of a living cell that was illuminated with a light pulse having a wavelength of about 280 nm and a duration of about 100 ms. The image information shown in FIG. 2 was captured using a microscopy device 100 similar to that shown in FIG. 1 in which a CCD 41 received light transmitted through the cell.

Of course, it will be understood that shorter pulse durations than 100 ms may be used, and may be preferable in reducing any adverse affect on the subject. Likewise, the illumination may have any suitable wavelength or combination of wavelengths within one or more ranges. In some embodiments, consecutive images or other image information may be captured for the same subject at intervals of 5 seconds, 10 seconds, 1 minute or more. It has been found, for example, that a living cell may be imaged using 280 nm light having a pulse duration of about 100 ms every minute for over 360 minutes without causing necrosis. Similarly, it has been found that a living cell may be imaged using 280 nm light having a pulse duration of about 100 ms every 10 seconds for about 40 minutes without causing necrosis.

2-dimensional image information that is captured using various aspects of the invention may be used in different ways to display and/or determine characteristics of a cell, biological material or other subject. Below, various imaging techniques and processes are described for determining several different characteristics of a cell, such as quantum yield, compound concentration or mass, optical density, and so on. It should be understood, however, that such techniques are not limited to use with a cell, but instead may be used with any suitable biological material or other subject.

Figure 3:
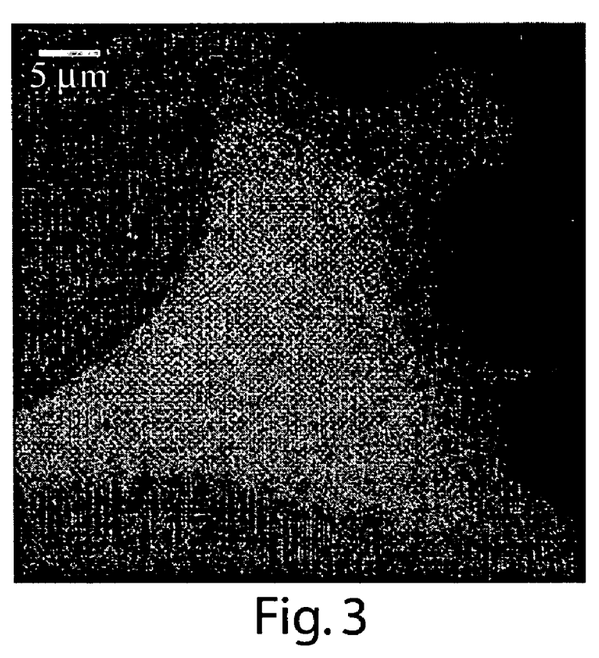
FIG. 3 shows an illustrative native fluorescence image of a fixed cell.
Figure 4:
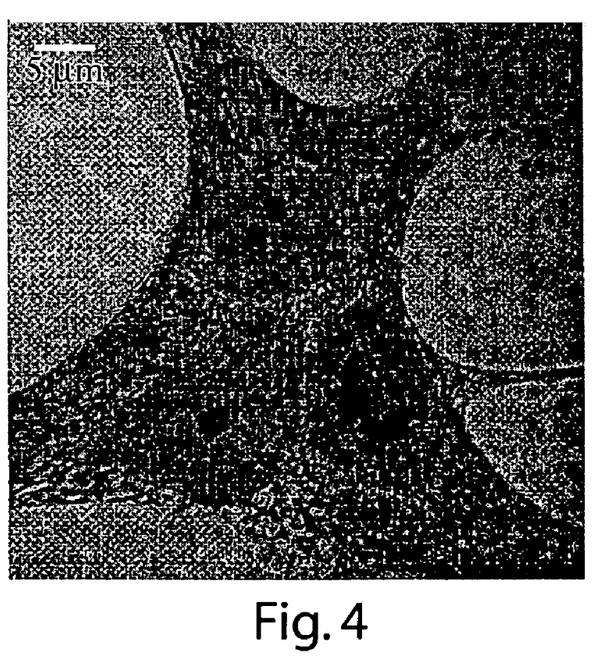
FIG. 4 shows an illustrative transmission image of the subject of FIG. 3.

In accordance with another aspect of the invention, a fluorescence image may be captured of a subject. For example, FIG. 3 shows an illustrative native fluorescence image of a-fixed cell. This image was captured using a microscopy device like that in FIG. 1 by first illuminating the subject with suitable illumination to excite a fluorophore in the subject, where the fluorophore in this particular case is tryptophan that is native to the cell. More generally, the fluorophore can be native to the subject or introduced to the subject (such as in the case of a stain, GFP, or other substance). The excited fluorophore emitted illumination that was detected by the detector 4 so as to capture the image shown in FIG. 3. With some native fluorophores, such as tryptophan, the subject may first be illuminated with light having a wavelength of about 280 nm, e.g., to capture the transmission image of FIG. 4. This illumination may excite tryptophan in the subject (e.g., a living cell), which causes the tryptophan to fluoresce or give off illumination having a wavelength of about 350 nm. This fluorescence illumination may be captured by the detector 4, e.g., by positioning a filter in the light path between the subject and the detector so as to allow the fluorescence light to pass to the detector 4, but block or attenuate the excitation illumination.

In accordance with one aspect of the invention, the subject may be illuminated using a diafluorescence arrangement in which the subject is illuminated so that light is transmitted through the subject to a detector. Using a diafluorescent illumination arrangement may allow an operator to illuminate the subject under identical conditions when capturing two or more different images, e.g., a transmission image and a fluorescence image, thereby allowing more accurate comparison of features elicited by the images. For example, the images of FIGS. 3 and 4 may be captured using identical illumination conditions provided by a diafluorescence illumination setup. To control the wavelength of light that reaches the detector 4, one or more filters may be used to filter light emanating from the subject. By using a filter having a pass band of about 280 nm (or possibly no filter at all), the detector may capture a transmission image like that in FIG. 4. Thereafter, a filter having a pass band of about the same wavelength at which the subject fluoresces may be introduced so that only (or mainly) fluorescent light reaches the detector to produce the image as in FIG. 3. Alternately, a dichroic filter and a second detector can be used to simultaneously acquire transmission and fluorescent images.

Figure 5:
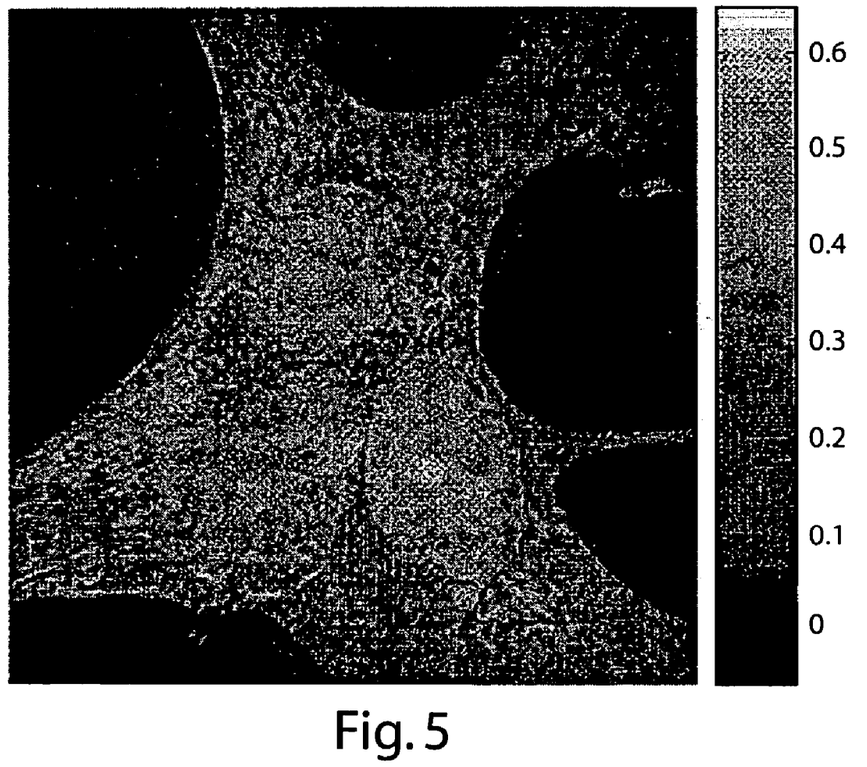
FIG. 5 shows an illustrative image of the optical density at 280 nm for the subject of FIG. 3.

In another aspect of the invention, an optical density of a subject may be determined based on one or more images of the subject, such as a background image captured with no subject located in a detector's field of view and a transmission image with the subject placed in the field of view. Based on a comparison of the two images, an optical density may be determined for one or more pixel or voxel locations of the subject. For example, FIG. 5 shows an illustrative image of an optical density at 280 nm, in the subject of FIG. 3. In this illustrative example, a background image was first captured by illuminating the field of view without the subject in the detector's field of view. This provides information regarding the light intensity in the field of view the absence of the subject. Thereafter, the subject was positioned in the field of view to capture the transmission image of FIG. 3. The optical density of the subject for various pixel or voxel locations may be determined, e.g., by the analyzer 5, by comparing the relative brightness in the background image and the transmission image. Contributions to the optical density by protein and by nucleic acid may be determined based on known relative or absolute concentrations of each compound for each pixel or voxel location. (An approach for determining such concentrations is discussed in more detail below.) Of course, those of skill in the art will appreciate that images of the type shown in FIG. 5 are not limited to protein and/or nucleic acid, but instead, optical density image representations may be generated for any suitable compound or collection of compounds by selection of appropriate wavelengths.

Figure 6:
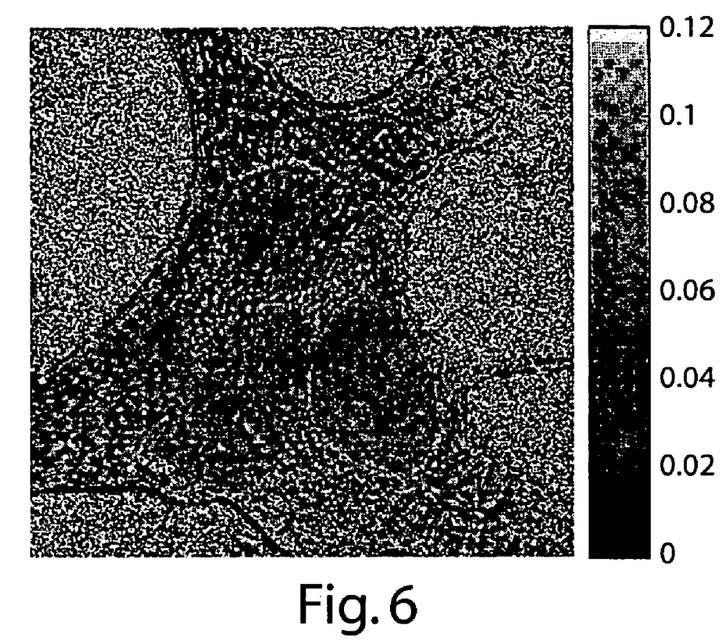
FIG. 6 shows an illustrative quantum yield image of the subject of FIG. 3.

In another aspect of the invention, one or more 2-dimensional images of a subject may be used to determine a quantum yield (i.e., a measure of how much light is re-emitted by one or more portions of the subject relative to how much light is absorbed by the subject) for the subject. The quantum yield may be determined on a pixel or voxel basis such that a quantum yield for multiple areas or regions in the subject may be determined. As is known in the art, for example, quantum yield characteristics can provide information regarding the molecular environment around a protein or other compound in a cell. FIG. 6 shows an illustrative quantum yield image that was determined for the subject of FIG. 3. This image may be generated by capturing a background image, then capturing a transmission image of the subject using an illumination wavelength that excites a fluorophore in the subject. For example, a living cell may be imaged using light having a wavelength of about 280 nm to generate a transmission image. As shown in Equation 1 below, the intensity Itrans for pixels in the transmission image is determined according to:

$$I\text{trans} = I_0 * 10^{-\epsilon c l} \quad (1)$$

where Io is an initial intensity obtained from the background image, $\epsilon$ is an extinction coefficient for the fluorophore, c is the concentration of the fluorophore, and l is the pathlength that the illumination traverses in the subject. After the transmission image is captured, a fluorescence image may be captured of the subject, e.g., in a way like that described above. As discussed above, a same field of illumination may be used for background, transmission and fluorescence images, allowing comparison of the images for an accurate determination of various characteristics, such as the quantum yield. Intensity values in the fluorescence image (Iaf) may be determined according to Equation 2:

$$Iaf = (\theta/360) * q * I_0 * (1 - 10^{-\epsilon cl}) \quad (2)$$

where θ is a collection angle in degrees for an objective in the microscopy device or other imaging arrangement and q is the quantum yield. Substitution of Equation 1 into Equation 2 and rearrangement yields Equation 3:

$$q = Iaf / ((\theta/360) * (I_0 - I_{trans})) \quad (3)$$

Thus, for each pixel, the quantum yield may be determined by dividing the fluorescence intensity by the difference between the initial intensity and the transmitted light intensity. This approach to determining quantum yield may be used with native fluorophores (i.e., compounds that have a native fluorescence, or autofluoresce, in response to an excitation illumination) or fluorophores that are artificially introduced (such as stains, marker or tag compounds, and so on).

In one illustrative embodiment, quantum yield may be determined for a living cell using tryptophan as a native fluorophore. Background, transmittance and fluorescence images may be obtained of the cell in a manner as discussed above, e.g., using an illumination wavelength of about 280 nm in a diafluorescence setup and identical illumination conditions for each image type. The fluorescence intensity Iaf is determined by Equation 4, which gives the quantum yield q for each pixel location:

$$Iaf = (\theta/360) * q * I0 * (1 - 10^{-ABStryptophan}) \quad (4)$$

where ABS(tryptophan) is the absorbance due to tryptophan. The absorbance may be determined based on an absolute concentration of tryptophan at each pixel location according to Equation 5 below.

$$ABS = \epsilon cl = \log_{10}(Io/T) \quad (5)$$

However, Equation 5 can only be used when the fluorophore of interest (in this case tryptophan) is the only significant absorber at the excitation wavelength, otherwise further processing must be done first to separate the ABS due to the fluorophore of interest from the total absorbance (described further below). Once quantum yield values are determined for one or more pixel locations, an image like that in FIG. 6 may be generated for display (e.g., by the analyzer 5). For example, different grayscale or color values may be associated with quantum yield values determined for each pixel so that a viewer of the generated image may readily appreciate differences in quantum yield in one portion of the subject as compared to the other.

In another aspect of the invention, concentrations of a compound in a subject may be determined based on one or more sets of image information. For example, using Equation 5 above, if the extinction coefficient ϵ is known for a compound in question, and a pathlength 1 (i.e., a distance through the subject that the illumination passes) is known, a concentration c of the compound may be determined from initial and measured illumination intensities obtained from a baseline and transmission image. Alternately, a mass of the compound may be determined on a voxel basis for the subject based on one or more sets of image information.

Again using Equation 5, once the absorbance for the subject is determined from a baseline and transmission image (and assuming that the extinction coefficient ϵ is known), the concentration*pathlength product (c*l) may be multiplied by a pixel area of the voxel (i.e., the pixel area for the voxel in the baseline and transmission images). (In this case, each voxel is a rectangular area that has a length equal to the pathlength 1.) This gives a total molar content of the compound in the voxel, which can be multiplied by a molar mass to yield a mass of the compound in grams.

While the approaches described above for determining concentration, mass, and quantum yield are effective when it is known that only a single compound contributes to the absorbance in a transmission image, a different approach may be required where two or more compounds are present in the subject. In accordance with another aspect of the invention, the concentrations of two or more different compounds may be determined based on two or more sets of image information. For example, the relative and absolute concentrations of protein and nucleic acid in a cell may be determined based on a baseline image, and two images obtained using different imaging conditions. In one illustrative embodiment, 280 nm excitation is used to acquire a transmission image and a native fluorescence image, and since both protein and nucleic acid absorb at 280 nm, but only protein fluoresces, by assuming a fixed quantum yield the relative and absolute concentrations of protein and nucleic acid can be determined. In another illustrative embodiment, two transmission images may be obtained for a subject using 260 nm light for one image and 280 nm light for another image. Since the absorption for any given pixel may be due in part to protein and in part to nucleic acid at these wavelengths, the composite absorption ABS at each pixel location (x,y) for a given wavelength may be given as in Equation 6:

$$ABS(x,y) = [\epsilon^{protein} * c^{protein}(x,y) + \epsilon^{nucleicacid} * c^{nucleicacid}(x,y)] * 1(x,y) \quad (6)$$

Figure 7:
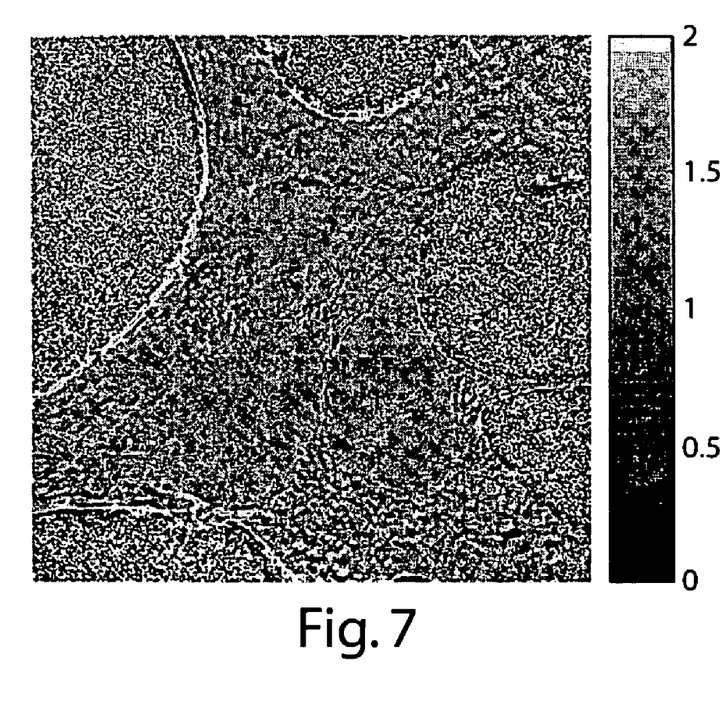
FIG. 7 shows an illustrative image depicting an absorbance ratio for the FIG. 3 subject regarding illumination at 260 nm and 280 nm.

The composite absorbance for each image may be determined in accordance with Equation 5, and if desired, the results may be used to generate one or more images for display. For example, FIG. 5 shows an illustrative image depicting an absorbance for the FIG. 3 subject for illumination at 280 nm, and FIG. 7 shows an illustrative image depicting an absorbance ratio for the FIG. 3 subject regarding illumination at 260 nm and 280 nm.

Figure 8:
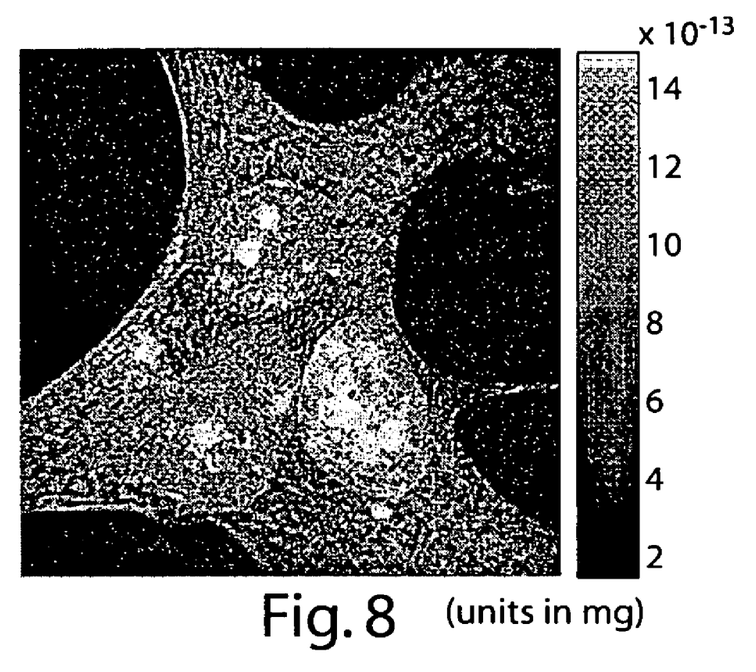
FIG. 8 shows an illustrative image depicting mass of DNA and RNA in the FIG. 3 subject.
Figure 9:
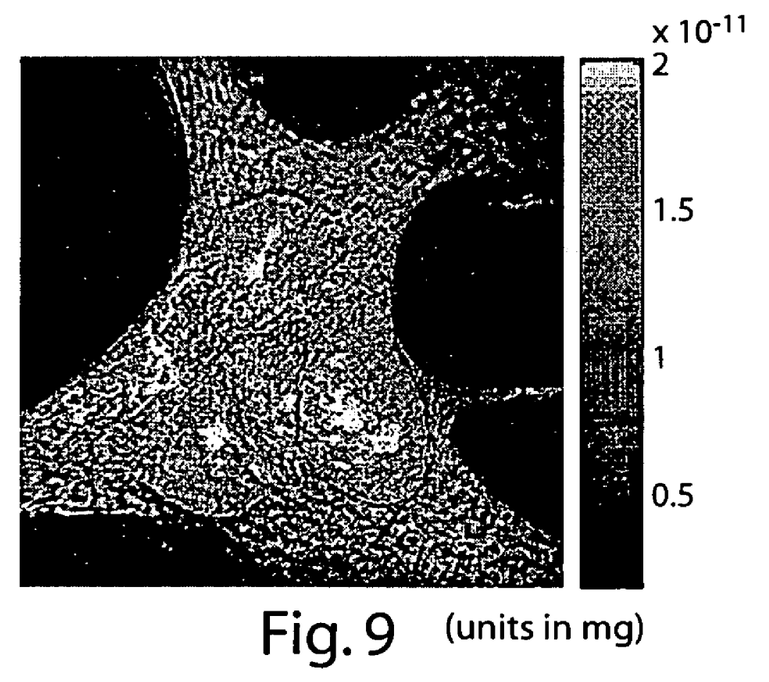
FIG. 9 shows an illustrative image depicting mass of protein in the FIG. 3 subject.

Since images may be obtained for two different illumination wavelengths, two equations of the form in Equation 6 may be determined—one for each image. Since only the concentrations c of the protein and nucleic acid may be unknown, the two equations may be used to solve for the two unknown concentration values. (Pathlength values 1 and extinction coefficients ϵ may be estimated or assumed based on the size of the cell being imaged and known extinction coefficients for DNA and RNA, and for tryptophan and tyrosine at the imaging wavelengths). Once determined, these concentrations may be used to generate one or more images for display of information. For example, FIG. 8 shows an illustrative image depicting the mass of DNA and RNA in the FIG. 3 subject, and FIG. 9 shows an illustrative image depicting the mass of protein in the FIG. 3 subject. As discussed above, concentration values may be used to display other information, such as optical density of a subject due to a specific protein or other compound, concentration, quantum yield for a particular compound, or for other purposes.

In another aspect of the invention, an illumination system for generating illumination suitable for circular dichroism and other analysis is provided. For example, an illumination system may include two light sources that each emit a light component that is linearly polarized in a direction perpendicular to the other component. The light sources may include a light emitter, such as an LED, lamp, laser or other, and one or more optical components, such as a collimator and other optics to polarize the light in a suitable way. The two light components provided by the light sources may be combined together, such as by a polarizing beam combiner, and then each component may be circularly polarized using optics such as a quarter-waveplate or fresnel rhomb such that one component is left circularly polarized and the other component is right circularly polarized. The result may be an illumination beam that includes left and right circularly polarized components. In one aspect of the invention, the two components may be modulated so as to have alternating minimum and maximum intensities that are 180 degrees out of phase with each other so that the illumination beam oscillates between left and right circularly polarized light at some frequency. Such an illumination beam may be useful in studying circular dichroism characteristics of a subject, e.g., in which the subject responds differently (whether through absorption or other characteristic) to left and right circularly polarized light. As is known in the art, such differences in response may indicate protein and DNA structure and other characteristics of interest.

Figure 10:
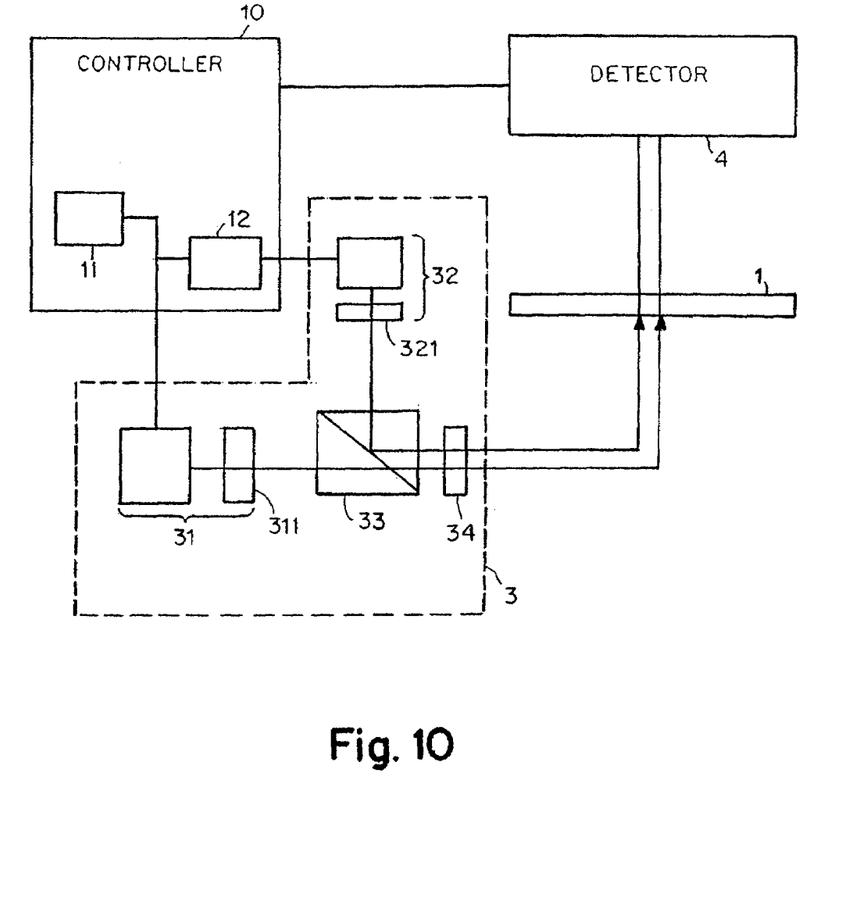
FIG. 10 shows a schematic diagram of an illumination system for producing a beam for circular dichroism analysis.

FIG. 10 shows a schematic diagram of an illumination system for producing a beam for circular dichroism analysis that may be used, for example, in the microscopy device of FIG. 1. It should be understood, however, that aspects of the illumination system may be used in other arrangements, such as in spectroscopy or other applications. In this illustrative embodiment, a first light source 31 includes an LED that emits a first light component having a wavelength of about 280 nm, although any suitable wavelength or range of wavelengths may be used. The first light source 31 also includes a collimator 311 to collimate the light from the LED, and a polarizer or other device that linearly polarizes the light. The second light source 32 includes similar elements, e.g., a collimator 321, and has a polarizer or other device that linearly polarizes a second light component from the LED in the second light source 32 in a direction orthogonal to the polarization of the light from the first light source 31, The two light components are combined together by a polarizing beam combiner, Glan-Taylor polarizer, or sharp-edged mirror 33, followed by optics that serve to circularly polarize each of the components, e.g., a quarter-wave plate 34 that has its fast axis aligned at about 45 degrees to the polarization directions of the two light components or a fresnel rhomb. The result is that one component is left circularly polarized, and the other component is right circularly polarized so as to form a beam that includes both left and right circularly polarized light.

Operation of the LEDs (or other suitable portions of the first and second light sources such as a mechanical chopper or shutter) may be controlled by the controller 10 so that the output of the first and second light sources is modulated to be intensity-wise 180 degrees out of phase. As a result, the combined light beam may oscillate between left and right circularly polarized light. The control signals used to control the output of the LEDs may be sinewave modulated or instead squarewave modulated so as to provide a sharper intensity rise and drop for the first and second light components. In one illustrative embodiment, the controller 10 includes an oscillator 11 that outputs a squarewave control signal to the first light source 31. An inverter 12 may invert the control signal and provide the inverted signal to the second light source 32 so that the second light source 32 outputs the second light component in a fashion that is intensity-wise 180 degrees out of phase with the first light component. The controller 10 may coordinate operation of the detector 4 so that image capture is synchronized with a particular phase of the light beam. For example, the controller 10 may control the detector 4 so that an image that is based only on right circularly polarized light is captured and/or so that an image that is based only on left circularly polarized light is captured. Alternately, the difference between the two signals can be detected directly as a fluctuation in signal at the modulation frequency—a measurement most effectively made using lock-in amplification techniques. Thus, the detector 4 may detect image information that is indicative of interaction of the subject with left or right circularly polarized light. These sets of image information may be compared and circular dichroism characteristics of the subject assessed. The frequency at which the combined beam intensity-wise oscillates between left and right circularly polarized light may be controlled based on the control signals provided to the first and second light sources 31 and 32. That is, in this embodiment, the frequency at which the combined beam oscillates is directly related to the frequency at which the control signals to the LEDs oscillates between on and off states. By controlling the frequency of the squarewave modulated signal to the LEDs, one can control the frequency at which the beam oscillates between left and right circularly polarized light.

As will be appreciated by those of skill in the art, illumination provided by an illumination system such as that in FIG. 10 may be used in a microscopy device to capture image information of various types. For example, transmission or fluorescence images resulting from interaction of left or right circularly polarized light with a subject may be captured. Moreover, such imaging may be combined with other aspects of the invention, such as those aspects relating to light pulse imaging, quantum yield or concentration determination, and so on. Thus, it should be understood that various aspects of the invention described herein may be used independently of other aspects of the invention, and/or in any suitable combination with other aspects of the invention.

The controller 10 may send and receive the signals to and from components in the device 100 in any suitable way, such as by wired and/or wireless link, and in any suitable format and/or communications protocol. The controller may include any suitable general purpose data processing system, which can be, or include, a suitably programmed general purpose computer, or network of general purpose computers, and other associated devices, including communication devices, and/or other circuitry or components necessary to perform the desired input/output or other functions. The controllers can also be implemented at least in part as single special purpose integrated circuits (e.g., ASICs), or an array of ASICs, each having a main or central processor section for overall, system-level control and separate sections dedicated to performing various different specific computations, functions and other processes under the control of the central processor section. The controller can also be implemented using a plurality of separate dedicated programmable integrated or other electronic circuits or devices, e.g., hardwired electronic or logic circuits, such as discrete element circuits or programmable logic devices. The controllers may also include other devices, such as an information display device, user input devices, such as a keyboard, user pointing device, touch screen or other user interface, data storage devices, communication devices or other electronic circuitry or components.

Having described several aspects of this invention, it should be appreciated that various alterations, modifications and improvements will occur to those of skill in the art. Such alterations, modifications and improvements are intended to be part of this disclosure and are intended to be within the spirit and scope of the invention. Thus, the description and drawings herein are intended to be illustrative, not limiting.

The invention claimed is:

1. An illumination system comprising:
   a first light source adapted to emit a first light component having a first linear polarization;
   a second light source adapted to emit second light component having a second linear polarization that is orthogonal to the first polarization;
   a controller adapted to provide control signals to the first and second light sources that cause the first and second light sources to emit the first and second light components so that the components are intensity-wise modulated 180 degrees out of phase relative to each other;
   an optical system that combines the first and second light components into a light beam and that circularly polarizes the first and second light components in opposite, left and right directions so that the light beam oscillates between left and right circular polarized light at a frequency.

2. The system of claim 1, wherein the first and second light sources include LEDs that emit light for the first and second light components.

3. The system of claim 1, wherein the controller includes a square wave oscillator that provides a first control signal to the first light emitting device, and an inverter that inverts the first control signal to form a second control signal that is provided to the second light emitting device.

4. The system of claim 1, wherein the frequency is adjustable.

5. The system of claim 1, wherein the optical system includes a quarter-wave plate or fresnel rhomb having its fast axis aligned at about 45 degrees to the first and second polarization directions.

6. The system of claim 1, wherein the first and second light sources each include a collimator that collimates the first and second light components, respectively.

7. The system of claim 1, incorporated into a microscopy device having a detector, wherein operation of the detector is synchronized with the frequency of the light beam.

8. The system of claim 1, wherein the first and second light components have a wavelength of less than 350 nm.

9. The system of claim 1, wherein the optical system includes a polarizing beam combiner that combines the first and second components into the light beam.

10. The system of claim 1, further comprising a detector whose operation is synchronized with the frequency of the light beam.

11. The system of claim 1, wherein the controller provides squarewave modulated control signals to the first and second light sources so that the first and second light components are intensity-wise squarewave modulated 180 degrees out of phase relative to each other.

12. A method for forming an illumination beam, comprising:
    providing a first light component having a first linear polarization and a first intensity-wise frequency;
    providing a second light component having a second linear polarization that is orthogonal to the first polarization and a second intensity-wise frequency that is 180 degrees out of phase with the first intensity-wise frequency;
    circularly polarizing the first and second light components to have opposite, left and right circular polarization; and
    combining the first and second light components into a light beam that intensity-wise oscillates between left and right circular polarized light at a frequency.

13. The method of claim 12, wherein the first and second light components are square wave modulated to have the first and second intensity-wise frequency.

14. The method of claim 12, wherein the step of circularly polarizing comprises transmitting the first and second components through a quarter-wave plate that has a fast axis oriented at 45 degrees to the first and second linear polarization directions.

15. The method of claim 12, wherein the steps of providing comprise controlling light emitting diodes to emit the first and second light components.

16. The method of claim 15, wherein the step of controlling comprises providing a square wave modulated control signal to the light emitting diodes.

17. The method of claim 12, wherein the first and second light components have a wavelength of less than 350 nm.

18. The method of claim 12, further comprising adjusting the frequency at which the light beam oscillates between left and right circularly polarized light.

19. The method of claim 12, further comprising synchronizing operation of a detector with the frequency of the light beam.

* * * * *